United States Patent
Lassila

(10) Patent No.: US 11,766,650 B2
(45) Date of Patent: Sep. 26, 2023

(54) SYSTEM AND METHOD TO PRODUCE PARTICLES OF ORGANIC SUBSTANCES

(71) Applicant: NANOFORM FINLAND OYJ, Helsinki (FI)

(72) Inventor: Ilkka Lassila, Helsinki (FI)

(73) Assignee: NANOFORM FINLAND OYJ, Helsinki (FI)

(*) Notice: Subject to any disclaimer, the term of this patent is extended or adjusted under 35 U.S.C. 154(b) by 0 days.

(21) Appl. No.: 17/796,189

(22) PCT Filed: Nov. 17, 2020

(86) PCT No.: PCT/FI2020/050769
§ 371 (c)(1),
(2) Date: Jul. 28, 2022

(87) PCT Pub. No.: WO2021/152204
PCT Pub. Date: Aug. 5, 2021

(65) Prior Publication Data
US 2023/0058525 A1 Feb. 23, 2023

(30) Foreign Application Priority Data
Jan. 29, 2020 (FI) ................................ 20205085

(51) Int. Cl.
*B01J 2/04* (2006.01)
*A61K 9/16* (2006.01)
*A61K 9/51* (2006.01)
*B01J 3/00* (2006.01)
*B01J 3/08* (2006.01)

(52) U.S. Cl.
CPC ............. *B01J 2/04* (2013.01); *A61K 9/1682* (2013.01); *A61K 9/5192* (2013.01); *B01J 3/008* (2013.01); *B01J 3/08* (2013.01)

(58) Field of Classification Search
CPC .... B01J 2/04; B01J 3/008; A61K 9/14; A61K 9/1682; A61K 9/5192
See application file for complete search history.

(56) References Cited

U.S. PATENT DOCUMENTS

| | | |
|---|---|---|
| 2002/0000681 A1 | 1/2002 | Gupta et al. |
| 2003/0157183 A1 | 8/2003 | Perrut |
| 2004/0071783 A1 | 4/2004 | Hanna et al. |

(Continued)

FOREIGN PATENT DOCUMENTS

| | | |
|---|---|---|
| CN | 101391156 | 3/2009 |
| WO | 2013/077459 | 5/2013 |
| WO | 2016/055696 | 4/2016 |

OTHER PUBLICATIONS

Piping and Instrumentation, Gemini Valve, https://www.geminivalve.com/pid-valve-symbols/, no date.*

(Continued)

*Primary Examiner* — Mary Lynn F Theisen
(74) *Attorney, Agent, or Firm* — NIXON & VANDERHYE

(57) ABSTRACT

Disclosed are systems and methods for producing particles of organic substances, in particular nanoparticles and microparticles of active pharmaceutical ingredients, wherein the particles are collected in the aid of an extension member engaged to a collection chamber and positioning a nozzle.

20 Claims, 3 Drawing Sheets

(56) References Cited

U.S. PATENT DOCUMENTS

| | | |
|---|---|---|
| 2006/0104916 A1 | 5/2006 | Shekunov et al. |
| 2012/0021021 A1 | 1/2012 | Deschamps et al. |
| 2014/0044819 A1 | 2/2014 | Demirbüker |
| 2017/0231914 A1 | 8/2017 | Haeggström et al. |
| 2018/0361627 A1* | 12/2018 | Merino Lopez .... B29B 17/0404 |

OTHER PUBLICATIONS

K. Byrappa et al., "Nanoparticles synthesis using supercritical fluid technology—towards biomedical applications", Advanced Drug Delivery Reviews, vol. 60, No. 3, Mar. 2008, pp. 299-327 (29 pages).
Search Report for FI Application No. 20205085 dated Aug. 20, 2020, 2 pages.
International Search Report for PCT/FI2020/050769 dated Mar. 1, 2021, 4 pages.
Written Opinion of the ISA for PCT/FI2020/050769 dated Mar. 1, 2021, 6 pages.
International Preliminary Report on Patentability for PCT/FI2020/050769 dated May 23, 2022, 5 pages.

* cited by examiner

SYSTEM AND METHOD TO PRODUCE PARTICLES OF ORGANIC SUBSTANCES

CROSS-REFERENCE TO RELATED APPLICATIONS

This application is the U.S. national phase of International Application No. PCT/FI2020/050769 filed Nov. 17, 2020 which designated the U.S. and claims priority to Finnish Patent Application No. 20205085 filed Jan. 29, 2020, the entire contents of each of which are hereby incorporated by reference.

BACKGROUND OF THE INVENTION

Field of the Invention

The present invention relates to systems and methods to produce particles of organic substances, in particular nano sized and micro sized active pharmaceutical ingredients in the aid of dry ice formation.

Description of the Related Art

In the pharmaceutical industry, large number of drugs are insoluble or poorly soluble in water, which leads to a low dissolution rates and thus also low bioavailability of the drugs. One solution is to reduce particle size which leads to an improvement of the dissolution behavior. The Rapid Expansion of Supercritical Solution (RESS) is among the most used methods. Controlled Expansion of Supercritical Solutions (CESS) in turn, represents an improvement over RESS technologies due to the employment of controlled mass transfer, flow and pressure reduction.

In a typical RESS process, supercritical fluid is used to dissolve solid material under high pressure and temperature, thus forming a homogeneous supercritical phase. Thereafter, the solution is expanded through a nozzle and small particles are formed.

A system suitable for production of micro- and nanoparticles of organic substances using RESS and CESS technologies is shown in FIG. 1. The system 100 comprises a pressure chamber 101 for a mixture of organic substance A and a supercritical carbon dioxide ($scCO_2$), a collection chamber 102, and an outlet tube 103 therebetween. The system comprises typically also one or more pressure controlling means 104 adapted to control pressure within the system, and a nozzle 105 adapted to allow expansion of the mixture from the outlet tube to the collection chamber.

When the mixture expands rapidly through a nozzle into ambient pressure, small particles a of the organic substance are formed, and solid $CO_2$ initially formed sublimates and exits the system via an exhaust vent 106. Since the nozzle is typically attached straight to the collection chamber, the particles are prone exit the collection chamber also.

Accordingly, there is need for further systems and methods to produce micro- and nanoparticles.

SUMMARY OF THE INVENTION

The following presents a simplified summary in order to provide a basic understanding of some aspects of various embodiments of the invention. The summary is not an extensive overview of the invention. It is neither intended to identify key nor critical elements of the invention, nor to delineate the scope of the invention. The following summary merely presents some concepts of the invention in a simplified form as a prelude to a more detailed description of exemplifying embodiments of the invention.

It was observed that when a system for producing particles of organic substances was equipped with an extension member between a nozzle and a collection chamber, loss of the particles of organic substances with gaseous $CO_2$ from the system could be avoided or at least alleviated.

Accordingly, it is an aspect of the present invention to provide a new system for producing particles of organic substances, the system comprising
- a pressure chamber for a mixture of the organic substances and supercritical carbon dioxide,
- a collection chamber,
- an outlet tube comprising a first end engaged to the pressure chamber and a second end,
- a nozzle engaged to the second end, and adapted to allow expansion of the mixture from the outlet tube towards the collection chamber, wherein the system comprises an extension member engaged to the outlet tube and the collection chamber and positioning the nozzle and wherein the system comprises a shutter comprising energy storing means such as spring-loaded shutter adapted to hold solid carbon dioxide comprising the particles of the organic substance in proximity of the nozzle and the extension member.

It is also an aspect of the present invention to provide a method for producing particles of organic substances using the disclosed system.

A number of exemplifying and non-limiting embodiments of the invention are also described and claimed.

Various exemplifying and non-limiting embodiments of the invention and to methods of operation, together with additional objects and advantages thereof, are best understood from the following description of specific exemplifying embodiments when read in connection with the accompanying figures.

The verbs "to comprise" and "to include" are used in this document as open limitations that neither exclude nor require the existence of also unrecited features. The features recited in depending claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

The exemplifying and non-limiting embodiments of the invention are explained in greater detail below with reference to the accompanying figures, in which.

DESCRIPTION OF THE PREFERRED EMBODIMENTS

The specific examples provided in the description given below should not be construed as limiting the scope and/or the applicability of the appended claims. Lists and groups of examples provided in the description given below are not exhaustive unless otherwise explicitly stated.

Figure 1:
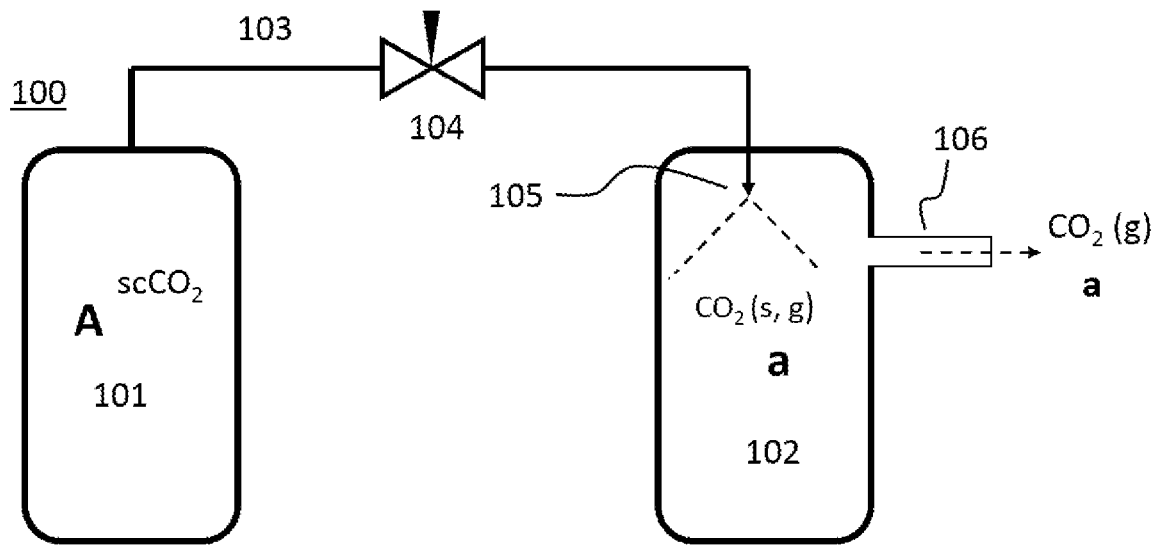
FIG. 1 shows system for producing particles of organic substance according to prior art.

System of FIG. 1 has been discussed in background section of the document.

Figure 2:
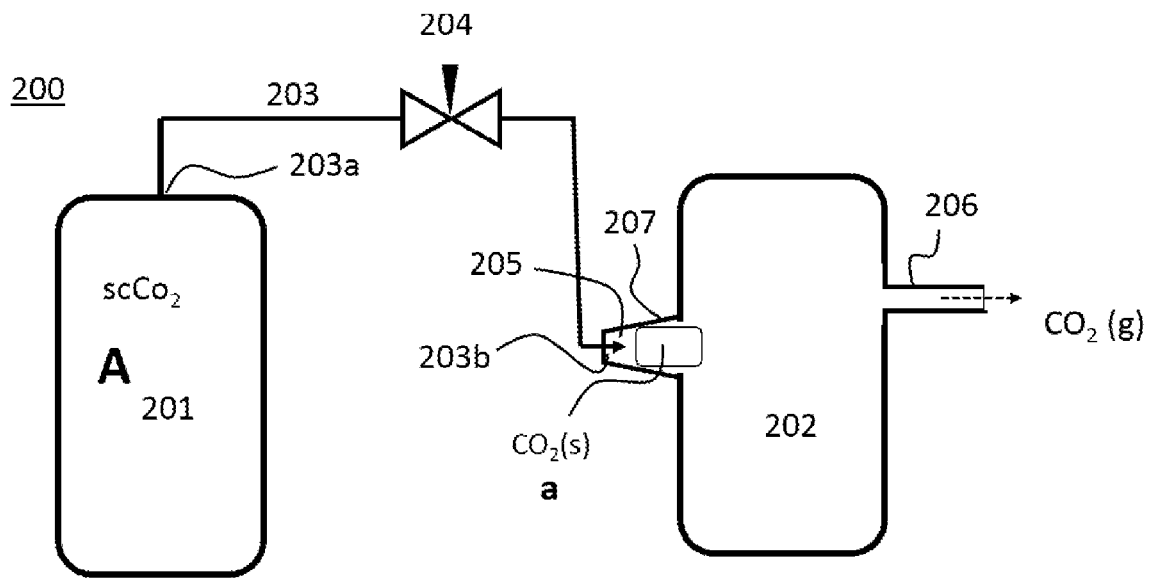
FIGS. 2-4 show exemplary non-limiting systems suitable for producing particles of organic substance according to embodiments of the present invention.

FIG. 2 illustrates a system 200 according to an exemplifying and non-limiting embodiment of the invention. The system comprises a pressure chamber 201 for a mixture of an organic substance A to be micronized or nanonised and supercritical carbon dioxide ($scCO_2$), a collection chamber 202 comprising an exit vent 206, an outlet tube 203 and a nozzle 205. First end 203a of the outlet tube is engaged to the pressure chamber and second end 203b of the outlet tube is engaged to the nozzle. The system comprises a pressure controlling means 204 (valve) adapted to control pressure of within the system.

The system comprises also an extension member 207 engaged to the outlet tube and the collection chamber. Outer surface of the extension member is preferably coated with insulating material. The nozzle is positioned within the extension member. The nozzle is adapted to allow expansion of the mixture from the outlet tube towards the collection chamber. When the system is in operation, solid carbon dioxide as snow comprising particles of the organic substance a is formed in the extension member. When the carbon dioxide snow sublimates, it exits the system via an exit vent 206 while the particles formed remain in the system.

Figure 3:
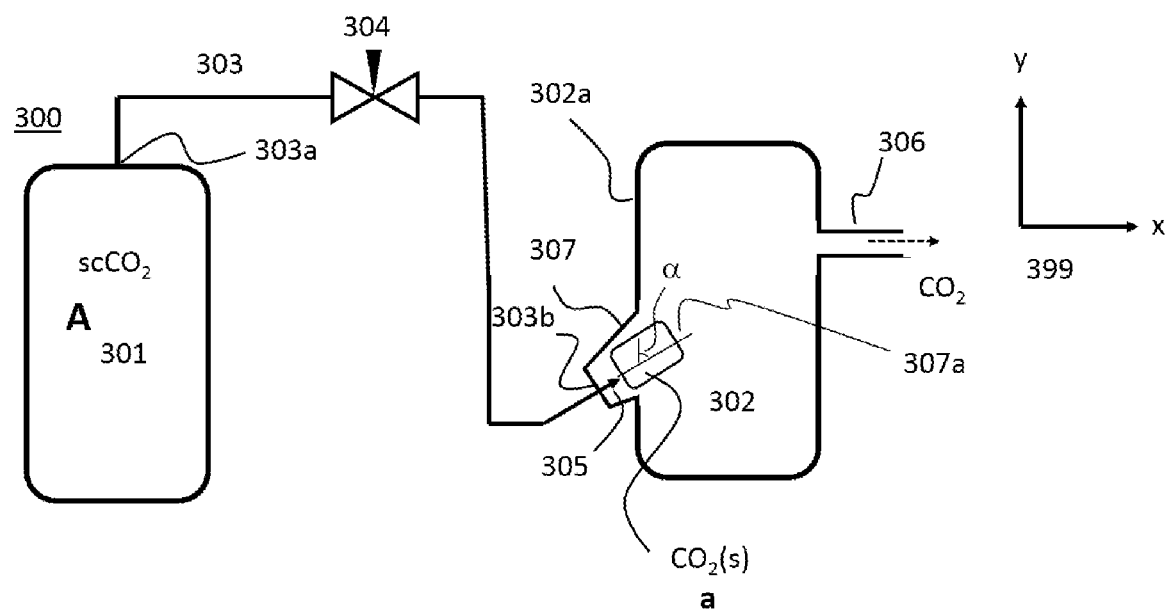

FIG. 3 illustrates another system 300 according to an exemplifying and non-limiting embodiment of the invention. The system comprises a pressure chamber 301 for a mixture of an organic substance A to be micro- or nanonised and supercritical carbon dioxide ($scCO_2$), a collection chamber 302 comprising an exit vent 306, an outlet tube 303 and a nozzle 305. First end 303a of the outlet tube is engaged to the pressure chamber and second end 303b of the outlet tube is engaged to the nozzle. The system comprises also a pressure controlling means 304 adapted to control pressure within the system. The system comprises an extension member 307 engaged to the outlet tube and the collection chamber. The nozzle is positioned within the extension member and is adapted to allow expansion of the mixture from the outlet tube towards the collection chamber. Central line 307a of the extension member is in an angle α in respect to the side wall 302a of the collection chamber so that gravity will assist to retain the $CO_2$ snow and the particles near the nozzle and the extension member, and thus further preventing the exit of the particles a from the collection chamber via the exit vent. The angle α is typically 10°-80°, wherein 0° and 90° is y-direction and x-direction of the coordinate system 399, respectively. An exemplary angle α is 45°. Accordingly, extension member is aligned substantially upwards when the system is at operating position.

Figure 4:
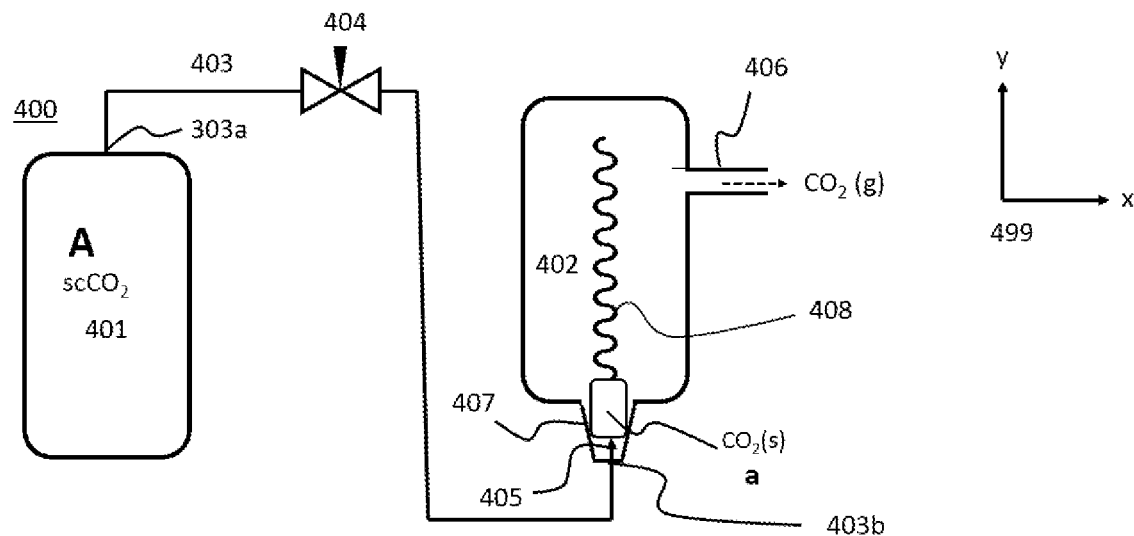

FIG. 4 illustrates another system 400 according to an exemplifying and non-limiting embodiment of the invention. The system comprises a pressure chamber 401 for a mixture of an organic substance A to be micronized or nanonised and supercritical carbon dioxide ($scCO_2$), a collection chamber 402 comprising an exit vent 406, an outlet tube 403 and a nozzle 405. First end 403a of the outlet tube is engaged to the pressure chamber and second end 403b of the outlet tube is engaged to the nozzle. The system comprises also a pressure controlling means 404 adapted to control pressure of within the system. The system comprises an extension member 407 engaged to the outlet tube and the collection chamber. The nozzle is positioned within the extension member and is adapted to allow expansion of the mixture from the outlet tube towards the collection chamber. The extension member is aligned so that it opens upwards i.e. in y-direction of the coordinate system 499 when the system is at its operating position. Accordingly, gravity will assist to retain the carbon dioxide snow near the nozzle and the extension member, and thus further diminish the exit of the particles a from the collection chamber.

The system 400 comprises also mechanical means 408 adapted to hold the carbon dioxide snow comprising the particles of organic substance in proximity of the nozzle and the extension member. Exemplary mechanical means are a screw conveyor and shutter comprising energy storing means, such as a spring-loaded shutter.

According to another embodiment the present invention concerns a method for producing particles of organic substances by using a system described above. According to an exemplary non-limiting embodiment the method comprises the following steps a) admixing organic substance with supercritical carbon dioxide in the pressure chamber 201, 301, 401 to form a mixture at a first pressure ($P_1$), b) passing the mixture through the outlet tube 203, 303, 403 towards the nozzle 205, 305, 405, c) forming solid carbon dioxide comprising particles of the organic substance by expanding the mixture to a final pressure ($P_F$) through the nozzle positioned in the extension member 206, 306, 406, d) collecting the solid carbon dioxide comprising particles of the organic substance within the extension member and e) allowing the solid carbon dioxide to sublimate.

According to a particular embodiment the step b) comprises decreasing the first pressure to a second pressure ($P_2$) during the passing. The decreasing is preferably gradual.

Step c) comprises decreasing the second pressure to the final pressure ($P_F$). The ratio ($P_1$)/($P_2$) and ($P_2/P_F$) is preferably <15, more preferably <10.

Pressure and temperature in the pressure chamber is such that the carbon dioxide is in supercritical state. The final pressure is typically atmospheric pressure. An exemplary temperature in the collection chamber is ambient temperature.

The particle size of organic substances obtained by the method of the present invention is typically 200 nm or less, preferably less than 100 nm, more preferably less than 50 nm, and most preferably less than 20 nm.

As defined herein a "nanoparticle" is a particle whose average diameter is 200 nm or less.

As defined herein an "organic substance" is a molecule containing carbon, excluding carbon containing alloys, and relatively small number of carbon-containing compounds such as metal carbonates and carbonyls, simple oxides of carbon and cyanides, as well as allotropes of carbon and simple carbon halides and sulfides which are considered inorganic. Exemplary organic substrates used in the present technology are biologically active materials including medicaments and their pharmaceutically acceptable organic and inorganic salts.

A non-limiting list of exemplary classes of biologically active materials are active pharmaceutical ingredients that may be of interest include analgesics, antagonists, anti-inflammatory agents, anthelmintics, antianginal agents, antiarrhythmic agents, antibiotics (including penicillins), anticholesterols, anticoagulants, anticonvulsants, antidepressants, antidiabetic agents, antiepileptics, antigonadotropins, antihistamines, antihypertensive agents, antimuscarinic agents, antimycobacterial agents, antineoplastic agents, antipsychotic agents, immunosuppressants, antithyroid agents, antiviral agents, antifungal agents, anxiolytic sedatives (hypnotics and neuroleptics), astringents, betaadrenoceptor blocking agents, blood products and substitutes, anti-cancer agents, cardiacinotropic agents, contrast media, corticosterioids, cough suppressants (expectorants and mucolytics), diuretics, dopaminergics (antiparkinsonian agents), haemostatics, immunosuppressive and immunoactive agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, vasidilators, neuron blocking agents, anticholinergic and cholinomimetic agents, antimuscarinic and muscarinic agents, vitamins, and xanthines.

The organic substances, such active pharmaceutical ingredient, may be crystallic, amorphic or their mixtures. According to one embodiment, the nanoparticles comprise active pharmaceutical ingredient and one or more excipients.

Exemplary active pharmaceutical ingredients suitable for the method of the present invention are entacapone, esomeprazole, atorvastatin, rabeprazole, piroxicam and olanzapine. An exemplary active pharmaceutical ingredient is piroxicam (4-hydroxy-2-methyl-N-(2-pyridinyl)-2H-1,2-benzothiazine-3-carboxamide 1,1-dioxide).

The combination of the extension member and the nozzle acting as a carbon dioxide snow horn well known in the art. A carbon dioxide snow horn is an orifice that allows expansion of liquid carbon dioxide.

Figure 5:
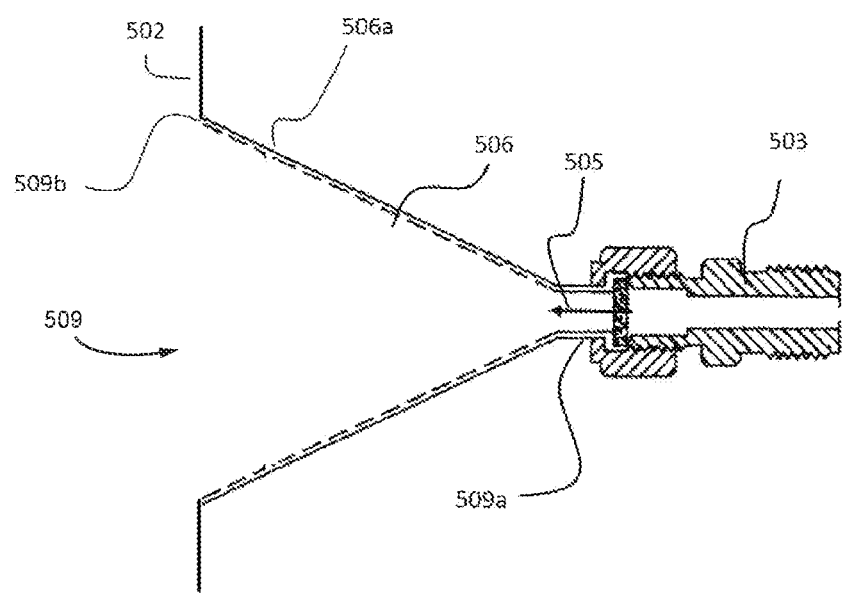
FIG. 5 shows an exemplary carbon dioxide snow horn suitable for the system and the method of the present invention.

According to another embodiment the present invention concerns new use of carbon dioxide snow horn as collecting means for particles of organic substances. An exemplary carbon dioxide snow horn 509 is shown in FIG. 5. The carbon dioxide snow horn comprises a nozzle 505, and an extension member 506. The outer surface 506a of the extension member is preferably coated with insulating material. The nozzle is positioned at the first end 509a of the carbon dioxide horn. When used in the system of the present invention, the first end 509a and the second end 509b of the snow horn is adapted to be engaged to a collection chamber 502 and an outlet tube 503, respectively. Shape of the extension member, type of the nozzle and size of the carbon dioxide snow horn can be modified according to the requirements of the system.

The specific examples provided in the description given above should not be construed as limiting the scope and/or the applicability of the appended claims.

What is claimed is:

1. A system for producing particles of organic substance, the system comprising
  a pressure chamber for a mixture of organic substance and supercritical carbon dioxide,
  a collection chamber,
  an outlet tube comprising a first end engaged to the pressure chamber and a second end,
  a nozzle engaged to the second end, and adapted to allow expansion of the mixture from the outlet tube towards the collection chamber,
  wherein the system comprises an extension member engaged to the collection chamber and to the outlet tube and positioning the nozzle and wherein the system comprises an energy storing means adapted to hold solid carbon dioxide comprising the particles of the organic substance in proximity of the nozzle and the extension member.

2. The system according to claim 1, wherein system comprises one or more valves adapted to control pressure in the system.

3. The system according to claim 1, wherein the collection chamber comprises an exit vent for carbon dioxide.

4. The system according to claim 1, wherein extension member is aligned substantially upwards when the system is at operating position.

5. A method for producing particles of organic substance by using the system according to claim 1, the method comprising the following steps
  a) admixing organic substance with supercritical carbon dioxide in the pressure chamber to form a mixture at a first pressure,
  b) passing the mixture through the outlet tube towards the nozzle,
  c) forming solid carbon dioxide comprising particles of the organic substance by expanding the mixture to a final pressure through the nozzle positioned in the extension member,
  d) collecting the solid carbon dioxide comprising particles of the organic substance within the extension member and
  e) allowing the solid carbon dioxide to sublimate.

6. The method according to claim 5, wherein step b) comprises decreasing the first pressure to a second pressure during the passing.

7. The method according to claim 6, wherein the decreasing is gradual.

8. The method according to claim 6, wherein step c) comprises decreasing the second pressure to the final pressure.

9. The method according to claim 6, wherein the second pressure is less than 100 bar.

10. The method according to claim 6, wherein ratio $P_1/P_2$ and $P_2/P_F$ is <15.

11. The method according to claim 5, wherein the final pressure is atmospheric pressure.

12. The method according to claim 5, wherein the particles are microparticles or nanoparticles.

13. The method according to claim 5, wherein the organic substance is an active pharmaceutical ingredient.

14. The system of claim 1, wherein the energy storing means is a spring-loaded shutter.

15. The method of claim 9, wherein the second pressure is 10-50 bar.

16. The method of claim 10, wherein the ratio $P_1/P_2$ and $P_2/P_F$ is <10.

17. The system according to claim 2, wherein the collection chamber comprises an exit vent for carbon dioxide.

18. The system according to claim 2, wherein extension member is aligned substantially upwards when the system is at operating position.

19. The system according to claim 3, wherein extension member is aligned substantially upwards when the system is at operating position.

20. A method for producing particles of organic substance by using the system according to claim 2, the method comprising the following steps
  a) admixing organic substance with supercritical carbon dioxide in the pressure chamber to form a mixture at a first pressure,
  b) passing the mixture through the outlet tube towards the nozzle,
  c) forming solid carbon dioxide comprising particles of the organic substance by expanding the mixture to a final pressure through the nozzle positioned in the extension member, d) collecting the solid carbon dioxide comprising particles of the organic substance within the extension member and
e) allowing the solid carbon dioxide to sublimate.

* * * * *